US008226568B2

(12) United States Patent
Watson et al.

(10) Patent No.: US 8,226,568 B2
(45) Date of Patent: Jul. 24, 2012

(54) SIGNAL PROCESSING SYSTEMS AND METHODS USING BASIS FUNCTIONS AND WAVELET TRANSFORMS

(75) Inventors: James Nicholas Watson, Dunfermline (GB); Paul Stanley Addison, Edinburgh (GB)

(73) Assignee: Nellcor Puritan Bennett LLC, Boulder, CO (US)

( * ) Notice: Subject to any disclaimer, the term of this patent is extended or adjusted under 35 U.S.C. 154(b) by 890 days.

(21) Appl. No.: 12/245,435

(22) Filed: Oct. 3, 2008

(65) Prior Publication Data

US 2010/0014724 A1    Jan. 21, 2010

Related U.S. Application Data

(60) Provisional application No. 61/080,897, filed on Jul. 15, 2008.

(51) Int. Cl.
*A61B 5/02* (2006.01)
*G06F 19/00* (2011.01)
*G06F 15/00* (2006.01)
*G11C 17/00* (2006.01)

(52) U.S. Cl. .................. 600/502; 702/19; 700/1; 365/94
(58) Field of Classification Search .......................... None
See application file for complete search history.

(56) References Cited

U.S. PATENT DOCUMENTS

| | | | |
|---|---|---|---|
| 4,289,141 A | 9/1981 | Cormier |
| 5,439,483 A | 8/1995 | Duong-Van |
| 5,590,650 A | 1/1997 | Genova |
| 5,632,272 A | 5/1997 | Diab et al. |
| 5,778,881 A | 7/1998 | Sun et al. |
| 5,795,304 A | 8/1998 | Sun et al. |
| 5,797,840 A | 8/1998 | Akselrod |
| 5,827,195 A | 10/1998 | Lander |
| 5,967,995 A | 10/1999 | Shusterman et al. |
| 6,002,952 A | 12/1999 | Diab et al. |
| 6,036,653 A | 3/2000 | Baba et al. |
| 6,094,592 A | 7/2000 | Yorkey |
| 6,095,984 A | 8/2000 | Amano et al. |
| 6,117,075 A | 9/2000 | Barnea |
| 6,129,675 A | 10/2000 | Jay |
| 6,135,966 A | 10/2000 | Ko |
| 6,171,257 B1 | 1/2001 | Weil et al. |
| 6,171,258 B1 | 1/2001 | Karakasoglu et al. |
| 6,208,951 B1 | 3/2001 | Kumar et al. |
| 6,293,915 B1 | 9/2001 | Amano et al. |
| 6,325,761 B1 | 12/2001 | Jay |
| 6,361,501 B1 | 3/2002 | Amano et al. |
| 6,393,311 B1 | 5/2002 | Edgar, Jr. et al. |
| 6,561,986 B2 | 5/2003 | Baura |
| 6,608,934 B2 | 8/2003 | Scheirer |
| 6,654,623 B1 | 11/2003 | Kastle |
| 6,810,277 B2 | 10/2004 | Edgar, Jr. et al. |
| 6,850,787 B2 | 2/2005 | Weber et al. |
| 6,931,269 B2 | 8/2005 | Terry |
| 7,001,337 B2 | 2/2006 | Dekker |
| 7,020,507 B2 | 3/2006 | Scharf |
| 7,035,679 B2 | 4/2006 | Addison |
| 7,043,293 B1 | 5/2006 | Baura |
| 7,054,453 B2 | 5/2006 | Causevic |
| 7,054,454 B2 | 5/2006 | Causevic et al. |
| 7,079,888 B2 | 7/2006 | Oung |
| 7,171,269 B1 | 1/2007 | Addison |
| 7,173,525 B2 | 2/2007 | Albert |
| 7,203,267 B2 | 4/2007 | De Man et al. |
| 7,225,013 B2 | 5/2007 | Geva et al. |
| 7,254,500 B2 | 8/2007 | Makeig |
| 7,289,835 B2 | 10/2007 | Mansfield |
| 7,373,194 B2 | 5/2008 | Weber et al. |
| 7,377,899 B2 | 5/2008 | Weber et al. |
| 7,467,002 B2 | 12/2008 | Weber et al. |
| 7,515,949 B2 | 4/2009 | Norris |
| 7,519,488 B2 | 4/2009 | Fu |
| 7,523,011 B2 | 4/2009 | Akiyama et al. |
| 2003/0163057 A1 | 8/2003 | Flick et al. |
| 2005/0043616 A1 | 2/2005 | Chinchoy |
| 2006/0209631 A1 | 9/2006 | Melese et al. |

(Continued)

FOREIGN PATENT DOCUMENTS

JP          09-084776       3/1997

(Continued)

OTHER PUBLICATIONS

Maja Bracic et al: "Wavelet-based analysis of human blood-flow dynamics", Bulletin of Mathematical Biology; A Journal Devoted to Research At the Junction of Computational, Theoretical and Experimental Biology, Springer-Verlag, NE, vol. 60, No. 5, Sep. 1, 1998, pp. 919-935, XP019416064, ISSN: 1522-9602, the whole document.
Addison, Paul S., The Illustrated Wavelet Transform Handbook, Taylor & Francis Group, 2002.
Addison, Paul, "The Little Wave with the Big Future," Physics World, Mar. 2004, pp. 35-39.
Clifton, David, Douglas, J. Graham, Addison, Paul S., Watson, James N., "Measurement of Respiratory Rate from the Photoplethysmogram in Chest Clinic Patients," Journal of Clinical Monitoring and Computing, 2006.
Leonard, Paul A., Douglas, J. Graham, Grubb, Neil R., Clifton, David, Addison, Paul S., Watson, James N., "A Fully Automated Algorithm for the Determination of Respiratory Rate From the Photoplethysmogram," Journal of Clinical Monitoring and Computing, 2006.

(Continued)

*Primary Examiner* — John S Brusca

(57) ABSTRACT

According to embodiments, systems and methods are provided that use continuous wavelet transforms and basis functions to provide an optimized system for the determination of physiological information. In an embodiment, the basis functions may be used to refine an area of interest in the signal in frequency or in time, and the continuous wavelet transform may be used to identify a maxima ridge in the scalogram at scales with characteristic frequencies proximal to the frequency or frequencies of interest. In another embodiment, a wavelet transform may be used to identify regions of a signal with the morphology of interest while basis functions may be used to focus on these regions to determine or filter information of interest. In yet another embodiment, basis functions and continuous wavelet transforms may be used concurrently and their results combined to form optimized information or a confidence metric for determined physiological information.

19 Claims, 12 Drawing Sheets

U.S. PATENT DOCUMENTS

| | | |
|---|---|---|
| 2006/0211930 A1 | 9/2006 | Scharf et al. |
| 2006/0229519 A1 | 10/2006 | Fujiwara et al. |
| 2006/0258921 A1 | 11/2006 | Addison et al. |
| 2006/0265022 A1 | 11/2006 | John et al. |
| 2007/0021673 A1 | 1/2007 | Arbel et al. |
| 2007/0073120 A1 | 3/2007 | Li et al. |
| 2007/0073124 A1 | 3/2007 | Li et al. |
| 2007/0167694 A1 | 7/2007 | Causevic et al. |
| 2007/0167851 A1 | 7/2007 | Vitali et al. |
| 2007/0282212 A1 | 12/2007 | Sierra et al. |
| 2008/0045832 A1 | 2/2008 | McGrath |
| 2008/0082018 A1 | 4/2008 | Sackner et al. |
| 2008/0214903 A1 | 9/2008 | Orbach |
| 2008/0243021 A1 | 10/2008 | Causevic et al. |

FOREIGN PATENT DOCUMENTS

| | | |
|---|---|---|
| WO | WO 01/25802 | 4/2001 |
| WO | WO 01/62152 | 8/2001 |
| WO | WO 03/055395 | 7/2003 |
| WO | WO 2004/105601 | 12/2004 |
| WO | WO 2005/096170 | 10/2005 |
| WO | WO 2006/085120 | 8/2006 |

OTHER PUBLICATIONS

Leonard, Paul A., Clifton, David, Addison, Paul S., Watson, James N., Beattie, Tom "An Automated Algorithm for Determining Respiratory Rate by Photoplethysmogram in Children," Acta Paediatricia, 2006; 95: 1124-1128.

Legarreta, I. Romero, Addison, P. S., Reed, M. J., Grubb, N. Clegg, G. R., Robertson, C. E., Watson, J. N., "Continuous Wavelet Transform Modulus Maxima Analysis of the Electrocardiogram: Beat Characterisation and Beat-to-Beat Measurement," International Journal of Wavelets, Multiresolution and Information Processing, vol. 3, No. 1, 2004, pp. 1-24.

Yamada, Michio, "Wavelet Analysis and Its Application," Journal of the Institute of Electronics, Information and Communication Engineers, vol. 76, No. 5, May 1993, pp. 518-528.

SIGNAL PROCESSING SYSTEMS AND METHODS USING BASIS FUNCTIONS AND WAVELET TRANSFORMS

CROSS REFERENCE TO RELATED APPLICATION

This claims the benefit of U.S. Provisional Application No. 61/080,897 filed Jul. 15, 2008, which is hereby incorporated by reference herein in its entirety.

SUMMARY

The present disclosure relates to signal processing systems and methods, and more particularly, to systems and methods for using basis functions and wavelet transforms to process signals.

Basis functions provide one technique for deriving physiological information from a physiological signal. Because basis functions can be represented using a limited number of coefficients, they can be easily applied to computations involving signals—for example, in signal compression. Basis functions typically have faster indexing and lower computational loads (at preselected indexes). In processing a photoplethysmogram (PPG) signal, basis functions may be particularly useful in refining the signal to focus on an area of interest. An area of interest in the PPG signal may be a particular frequency or range of frequencies about a unique characteristic within the signal, such as a frequency or range of frequencies about an estimate of the pulse rate. Alternatively, an area of interest in the PPG signal may be a particular time or range of time about a unique event in the signal, such as a time in which physiological information is measured. A set of basis functions may be chosen according to the area of interest such that when the basis functions are subtracted from the PPG signal, the information in the area of interest becomes more refined or pronounced. Such a cancellation process may allow the signal of interest to be further processed to more accurately determine physiological information, such as oxygen saturation.

Continuous wavelet transforms may also provide a convenient method of calculating physiological information from a physiological signal. Continuous wavelet transforms may provide good feature identification and denoising strengths (at preselected scales and time). Thus, in processing a PPG signal continuous wavelet transforms may be particularly useful to locate a maxima ridge in the scalogram from which to determine physiological information, such as oxygen saturation.

Collectively, continuous wavelet transforms and basis functions may provide an optimized determination of physiological information. Continuous wavelet transforms and basis function processing may be applied to received signals in serial. An area of interest in scale or time in the signal may be processed by the continuous wavelet transforms and basis function processing. Using continuous wavelet transforms on the received signals before basis function processing may yield certain advantages, such as more precise maxima ridge calculation. However, using basis function processing on the received signals before continuous wavelet transforms may provide better filtering of noise from the signal. Alternatively, continuous wavelet transforms and basis function processing may be performed concurrently on received signals. The results of each process may be compared in order to calculate physiological information more accurately.

In an embodiment, the basis functions may be used to refine an area of interest in frequency or in time in the signal, and the continuous wavelet transform may be used to identify a maxima ridge in the scalogram proximal to the area of interest. For example, a sinusoidal basis set may be generated, and an iterative cancellation procedure about an area of interest may be used to identify a nominal frequency of interest for the calculation of physiological information. A wavelet transform may then be performed at scales with characteristic frequencies about this frequency of interest. The maxima ridge in the scalogram proximal to these scales of interest may then be used to calculate physiological information.

In one embodiment, a wavelet transform may be used to identify regions of a signal with the morphology of interest while basis functions may be used to focus on these regions to determine or filter information of interest. For example, a wavelet transform may be performed about an area of interest in scale or in time in the signal. A sinusoidal basis set may be generated, and an iterative cancellation procedure about the identified area of interest may then be used to determine physiological information.

In one embodiment, basis functions and continuous wavelet transforms may be used concurrently and their results combined to determine optimized information or a confidence metric for determined physiological information. For example, the basis function processing and wavelet transform may be performed on the received signals in parallel about an area of interest in scale or in time in the signal. The results of each method may be combined and analyzed to determine optimized physiological information, as well as confidence measures corresponding to the determination of physiological information.

BRIEF DESCRIPTION OF THE DRAWINGS

The above and other features of the present disclosure, its nature and various advantages will be more apparent upon consideration of the following detailed description, taken in conjunction with the accompanying drawings in which.

DETAILED DESCRIPTION

Figure 1:
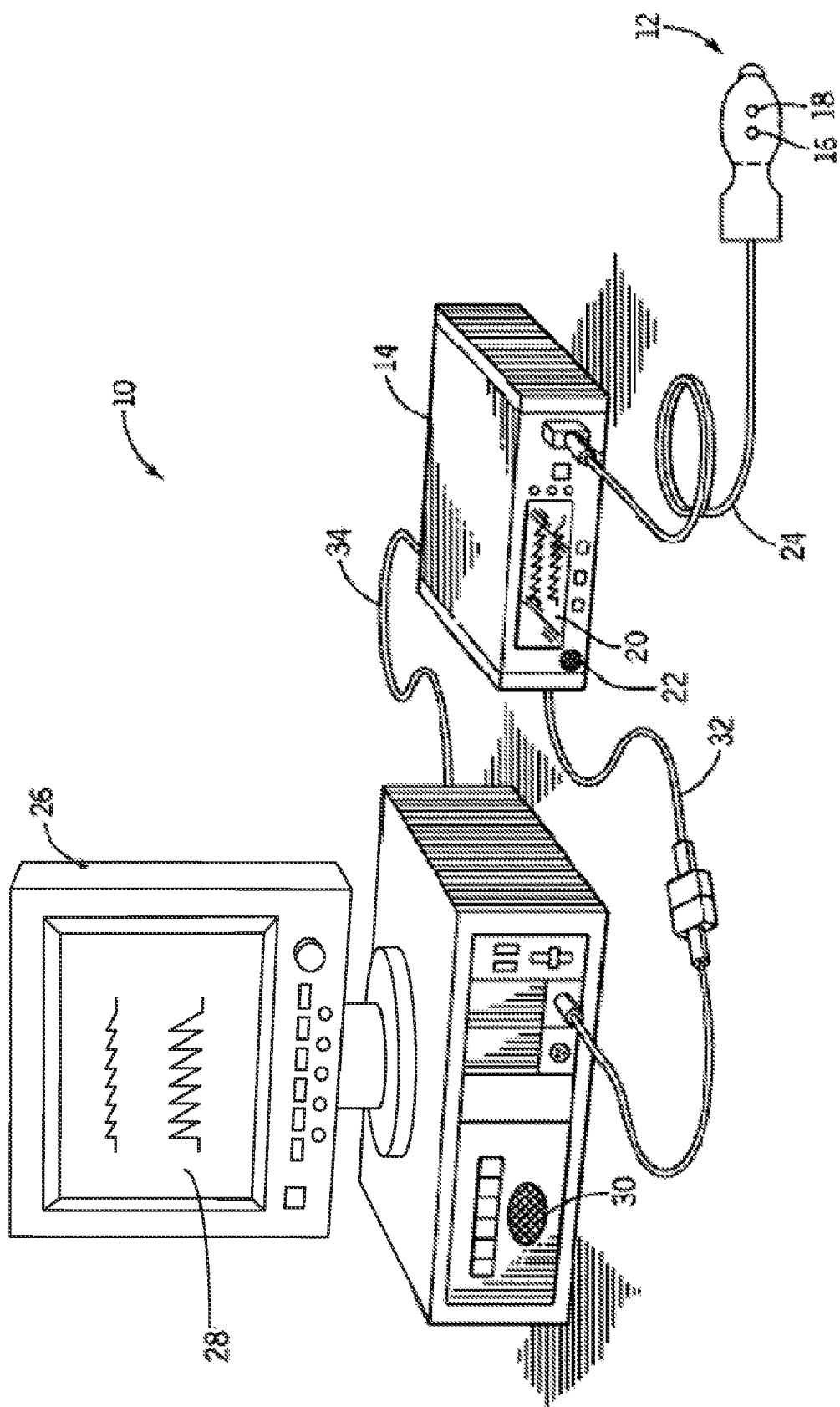
FIG. 1 shows an illustrative pulse oximetry system in accordance with an embodiment.

An oximeter is a medical device that may determine the oxygen saturation of the blood. One common type of oximeter is a pulse oximeter, which may indirectly measure the oxygen saturation of a patient's blood (as opposed to measuring oxygen saturation directly by analyzing a blood sample taken from the patient) and changes in blood volume in the skin. Ancillary to the blood oxygen saturation measurement, pulse oximeters may also be used to measure the pulse rate of the patient. Pulse oximeters typically measure and display various blood flow characteristics including, but not limited to, the oxygen saturation of hemoglobin in arterial blood.

An oximeter may include a light sensor that is placed at a site on a patient, typically a fingertip, toe, forehead or earlobe, or in the case of a neonate, across a foot. The oximeter may pass light using a light source through blood perfused tissue and photoelectrically sense the absorption of light in the tissue. For example, the oximeter may measure the intensity of light that is received at the light sensor as a function of time. A signal representing light intensity versus time or a mathematical manipulation of this signal (e.g., a scaled version thereof, a log taken thereof, a scaled version of a log taken thereof, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to calculate the amount of the blood constituent (e.g., oxyhemoglobin) being measured as well as the pulse rate and when each individual pulse occurs.

The light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption. Red and infrared wavelengths may be used because it has been observed that highly oxygenated blood will absorb relatively less red light and more infrared light than blood with a lower oxygen saturation. By comparing the intensities of two wavelengths at different points in the pulse cycle, it is possible to estimate the blood oxygen saturation of hemoglobin in arterial blood.

When the measured blood parameter is the oxygen saturation of hemoglobin, a convenient starting point assumes a saturation calculation based on Lambert-Beer's law. The following notation will be used herein:

$$I(\lambda,t)=I_o(\lambda)\exp(-(s\beta_o(\lambda)+(1-s)\beta_r(\lambda))l(t)) \quad (1)$$

where:
$\lambda$=wavelength;
t=time;
I=intensity of light detected;
$I_o$=intensity of light transmitted;
s=oxygen saturation;
$\beta_o$, $\beta_r$=empirically derived absorption coefficients; and
l(t)=a combination of concentration and path length from emitter to detector as a function of time.

The traditional approach measures light absorption at two wavelengths (e.g., red and infrared (IR)), and then calculates saturation by solving for the "ratio of ratios" as follows.

1. First, the natural logarithm of (1) is taken ("log" will be used to represent the natural logarithm) for IR and Red $$\log I = \log I_o - (s\beta_o + (1-s)\beta_r)l \quad (2)$$

2. (2) is then differentiated with respect to time $$\frac{d\log I}{dt} = -(s\beta_o + (1-s)\beta_r)\frac{dl}{dt} \quad (3)$$

3. Red (3) is divided by IR (3)

$$\frac{d\log I(\lambda_R)/dt}{d\log I(\lambda_{IR})/dt} = \frac{s\beta_o(\lambda_R)+(1-s)\beta_r(\lambda_R)}{s\beta_o(\lambda_{IR})+(1-s)\beta_r(\lambda_{IR})} \quad (4)$$

4. Solving for s $$s = \frac{\frac{d\log I(\lambda_{IR})}{dt}\beta_r(\lambda_R) - \frac{d\log I(\lambda_R)}{dt}\beta_r(\lambda_{IR})}{\frac{d\log I(\lambda_R)}{dt}(\beta_o(\lambda_{IR})-\beta_r(\lambda_{IR})) - \frac{d\log I(\lambda_{IR})}{dt}(\beta_o(\lambda_R)-\beta_r(\lambda_R))}$$

Note in discrete time $$\frac{d\log I(\lambda,t)}{dt} \simeq \log I(\lambda, t_2) - \log I(\lambda, t_1)$$

Using log A−log B=log A/B, $$\frac{d\log I(\lambda,t)}{dt} \simeq \log\left(\frac{I(t_2,\lambda)}{I(t_1,\lambda)}\right)$$

So, (4) can be rewritten as $$\frac{\frac{d\log I(\lambda_R)}{dt}}{\frac{d\log I(\lambda_{IR})}{dt}} \simeq \frac{\log\left(\frac{I(t_1,\lambda_R)}{I(t_2,\lambda_R)}\right)}{\log\left(\frac{I(t_1,\lambda_{IR})}{I(t_2,\lambda_{IR})}\right)} = R \quad (5)$$

where R represents the "ratio of ratios." Solving (4) for s using (5) gives $$s = \frac{\beta_r(\lambda_R) - R\beta_r(\lambda_{IR})}{R(\beta_o(\lambda_{IR})-\beta_r(\lambda_{IR}))-\beta_o(\lambda_R)+\beta_r(\lambda_R)}.$$

From (5), R can be calculated using two points (e.g., PPG maximum and minimum), or a family of points. One method using a family of points uses a modified version of (5). Using the relationship $$\frac{d\log I}{dt} = \frac{dI/dt}{I} \quad (6)$$

now (5) becomes $$\frac{\frac{d\log I(\lambda_R)}{dt}}{\frac{d\log I(\lambda_{IR})}{dt}} \simeq \frac{\frac{I(t_2,\lambda_R) - I(t_1,\lambda_R)}{I(t_1,\lambda_R)}}{\frac{I(t_2,\lambda_{IR}) - I(t_1,\lambda_{IR})}{I(t_1,\lambda_{IR})}} \quad (7)$$

$$= \frac{[I(t_2,\lambda_R) - I(t_1,\lambda_R)]I(t_1,\lambda_{IR})}{[I(t_2,\lambda_{IR}) - I(t_1,\lambda_{IR})]I(t_1,\lambda_R)}$$

$$= R$$

which defines a cluster of points whose slope of y versus x will give R where $$x(t) = [I(t_2,\lambda_{IR}) - I(t_1,\lambda_{IR})]I(t_1,\lambda_R) \quad (8)$$

$$y(t) = [I(t_2,\lambda_R) - I(t_1,\lambda_R)]I(t_1,\lambda_{IR})$$

$$y(t) = Rx(t)$$

FIG. 1 is a perspective view of an embodiment of a pulse oximetry system 10. System 10 may include a sensor 12 and a pulse oximetry monitor 14. Sensor 12 may include an emitter 16 for emitting light at two or more wavelengths into a patient's tissue. A detector 18 may also be provided in sensor 12 for detecting the light originally from emitter 16 that emanates from the patient's tissue after passing through the tissue.

According to another embodiment and as will be described, system 10 may include a plurality of sensors forming a sensor array in lieu of single sensor 12. Each of the sensors of the sensor array may be a complementary metal oxide semiconductor (CMOS) sensor. Alternatively, each sensor of the array may be charged coupled device (CCD) sensor. In another embodiment, the sensor array may be made up of a combination of CMOS and CCD sensors. The CCD sensor may comprise a photoactive region and a transmission region for receiving and transmitting data whereas the CMOS sensor may be made up of an integrated circuit having an array of pixel sensors. Each pixel may have a photodetector and an active amplifier.

According to an embodiment, emitter 16 and detector 18 may be on opposite sides of a digit such as a finger or toe, in which case the light that is emanating from the tissue has passed completely through the digit. In an embodiment, emitter 16 and detector 18 may be arranged so that light from emitter 16 penetrates the tissue and is reflected by the tissue into detector 18, such as a sensor designed to obtain pulse oximetry data from a patient's forehead.

In an embodiment, the sensor or sensor array may be connected to and draw its power from monitor 14 as shown. In another embodiment, the sensor may be wirelessly connected to monitor 14 and include its own battery or similar power supply (not shown). Monitor 14 may be configured to calculate physiological parameters based at least in part on data received from sensor 12 relating to light emission and detection. In an alternative embodiment, the calculations may be performed on the monitoring device itself and the result of the oximetry reading may be passed to monitor 14. Further, monitor 14 may include a display 20 configured to display the physiological parameters or other information about the system. In the embodiment shown, monitor 14 may also include a speaker 22 to provide an audible sound that may be used in various other embodiments, such as for example, sounding an audible alarm in the event that a patient's physiological parameters are not within a predefined normal range.

In an embodiment, sensor 12, or the sensor array, may be communicatively coupled to monitor 14 via a cable 24. However, in other embodiments, a wireless transmission device (not shown) or the like may be used instead of or in addition to cable 24.

In the illustrated embodiment, pulse oximetry system 10 may also include a multi-parameter patient monitor 26. The monitor may be cathode ray tube type, a flat panel display (as shown) such as a liquid crystal display (LCD) or a plasma display, or any other type of monitor now known or later developed. Multi-parameter patient monitor 26 may be configured to calculate physiological parameters and to provide a display 28 for information from monitor 14 and from other medical monitoring devices or systems (not shown). For example, multiparameter patient monitor 26 may be configured to display an estimate of a patient's blood oxygen saturation generated by pulse oximetry monitor 14 (referred to as an "SpO$_2$" measurement), pulse rate information from monitor 14 and blood pressure from a blood pressure monitor (not shown) on display 28.

Monitor 14 may be communicatively coupled to multi-parameter patient monitor 26 via a cable 32 or 34 that is coupled to a sensor input port or a digital communications port, respectively and/or may communicate wirelessly (not shown). In addition, monitor 14 and/or multi-parameter patient monitor 26 may be coupled to a network to enable the sharing of information with servers or other workstations (not shown). Monitor 14 may be powered by a battery (not shown) or by a conventional power source such as a wall outlet.

Figure 2:
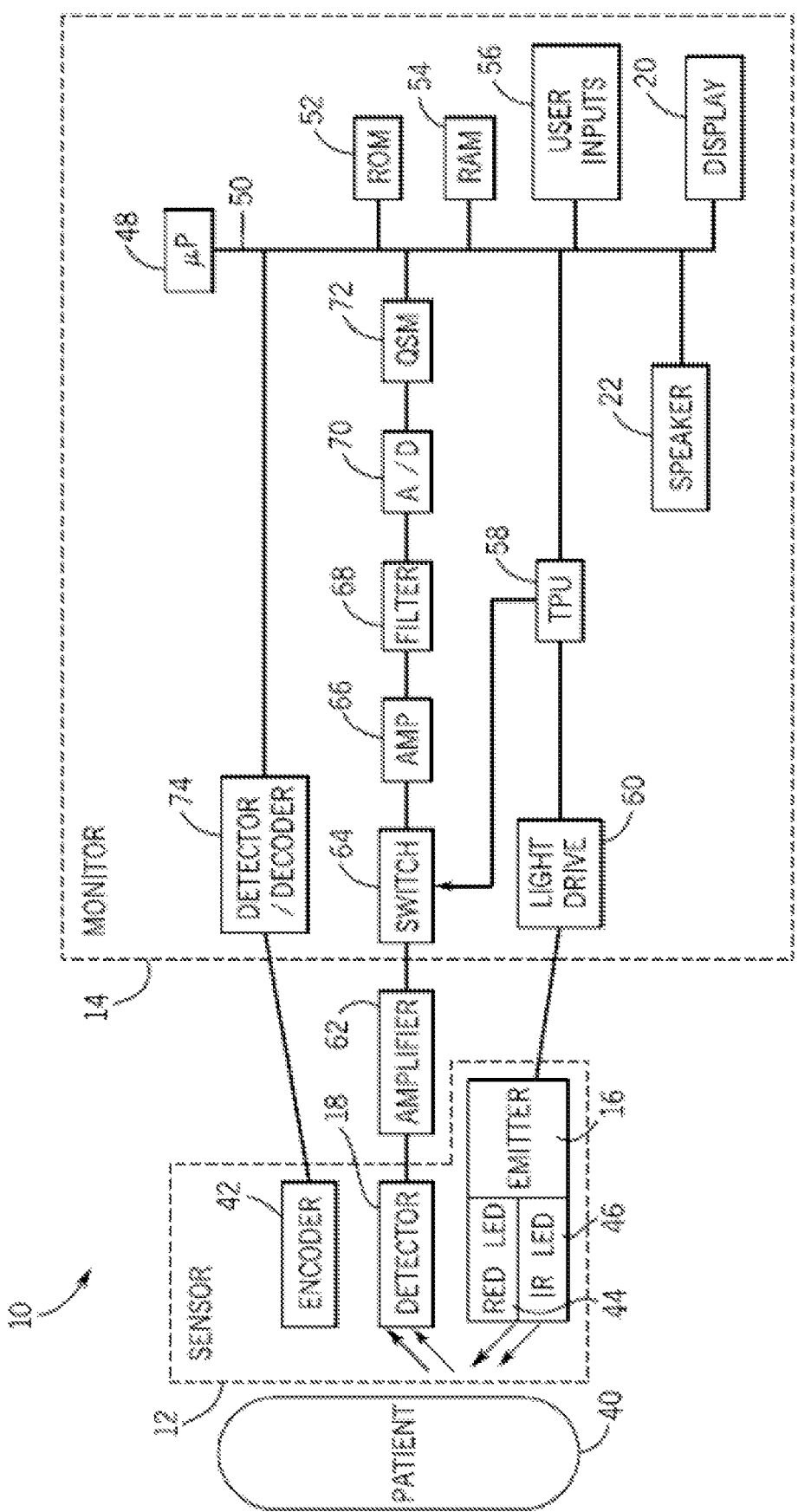
FIG. 2 is a block diagram of the illustrative pulse oximetry system of FIG. 1 coupled to a patient in accordance with an embodiment.

FIG. 2 is a block diagram of a pulse oximetry system, such as pulse oximetry system 10 of FIG. 1, which may be coupled to a patient 40 in accordance with an embodiment. Certain illustrative components of sensor 12 and monitor 14 are illustrated in FIG. 2. Sensor 12 may include emitter 16, detector 18, and encoder 42. In the embodiment shown, emitter 16 may be configured to emit at least two wavelengths of light (e.g., RED and IR) into a patients tissue 40. Hence, emitter 16 may include a RED light emitting light source such as RED light emitting diode (LED) 44 and an IR light emitting light source such as IR LED 46 for emitting light into the patient's tissue 40 at the wavelengths used to calculate the patients physiological parameters. In one embodiment, the RED wavelength may be between about 600 nm and about 700 nm, and the IR wavelength may be between about 800 nm and about 1000 nm. In embodiments where a sensor array is used in place of single sensor, each sensor may be configured to emit a single wavelength. For example, a first sensor emits only a RED light while a second only emits an IR light.

It will be understood that, as used herein, the term "light" may refer to energy produced by radiative sources and may include one or more of ultrasound, radio, microwave, millimeter wave, infrared, visible, ultraviolet, gamma ray or X-ray electromagnetic radiation. As used herein, light may also include any wavelength within the radio, microwave, infrared, visible, ultraviolet, or X-ray spectra, and that any suitable wavelength of electromagnetic radiation may be appropriate for use with the present techniques. Detector 18 may be chosen to be specifically sensitive to the chosen targeted energy spectrum of the emitter 16.

In an embodiment, detector 18 may be configured to detect the intensity of light at the RED and IR wavelengths. Alternatively, each sensor in the array may be configured to detect an intensity of a single wavelength. In operation, light may enter detector 18 after passing through the patient's tissue 40. Detector 18 may convert the intensity of the received light into an electrical signal. The light intensity is directly related to the absorbance and/or reflectance of light in the tissue 40. That is, when more light at a certain wavelength is absorbed or reflected, less light of that wavelength is received from the tissue by the detector 18. After converting the received light to an electrical signal detector 18 may send the signal to monitor 14, where physiological parameters may be calculated based on the absorption of the RED and IR wavelengths in the patient's tissue 40.

In an embodiment, encoder 42 may contain information about sensor 12, such as what type of sensor it is (e.g., whether the sensor is intended for placement on a forehead or digit) and the wavelengths of light emitted by emitter 16. This information may be used by monitor 14 to select appropriate algorithms, lookup tables and/or calibration coefficients stored in monitor 14 for calculating the patient's physiological parameters.

Encoder 42 may contain information specific to patient 40, such as, for example, the patients age, weight, and diagnosis. This information may allow monitor 14 to determine, for example, patient-specific threshold ranges in which the patient's physiological parameter measurements should fall and to enable or disable additional physiological parameter algorithms. Encoder 42 may, for instance, be a coded resistor which stores values corresponding to the type of sensor 12 or the type of each sensor in the sensor array, the wavelengths of light emitted by emitter 16 on each sensor of the sensor array, and/or the patient's characteristics. In another embodiment, encoder 42 may include a memory on which one or more of the following information may be stored for communication to monitor 14; the type of the sensor 12; the wavelengths of light emitted by emitter 16; the particular wavelength each sensor in the sensor array is monitoring; a signal threshold for each sensor in the sensor array; any other suitable information; or any combination thereof.

In an embodiment, signals from detector 18 and encoder 42 may be transmitted to monitor 14. In the embodiment shown, monitor 14 may include a general-purpose microprocessor 48 connected to an internal bus 50. Microprocessor 48 may be adapted to execute software, which may include an operating system and one or more applications, as part of performing the functions described herein. Also connected to bus 50 may be a read-only memory (ROM) 52, a random access memory (RAM) 54, user inputs 56, display 20, and speaker 22.

RAM 54 and ROM 52 are illustrated by way of example, and not limitation. Any suitable computer-readable media may be used in the system for data storage. Computer-readable media are capable of storing information that can be interpreted by microprocessor 48. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

In the embodiment shown, a time processing unit (TPU) 58 may provide timing control signals to a light drive circuitry 60, which may control when emitter 16 is illuminated and multiplexed timing for the RED LED 44 and the IR LED 46. TPU 58 may also control the gating-in of signals from detector 18 through an amplifier 62 and a switching circuit 64. These signals are sampled at the proper time, depending upon which light source is illuminated. The received signal from detector 18 may be passed through an amplifier 66, a low pass filter 68, and an analog-to-digital converter 70. The digital data may then be stored in a queued serial module (QSM) 72 (or buffer) for later downloading to RAM 54 as QSM 72 fills up. In one embodiment) there may be multiple separate parallel paths having amplifier 66, filter 68, and A/D converter 70 for multiple light wavelengths or spectra received.

In an embodiment, microprocessor 48 may determine the patient's physiological parameters, such as $SPO_2$ and pulse rate, using various algorithms and/or look-up tables based on the value of the received signals and/or data corresponding to the light received by detector 18. Signals corresponding to information about patient 40, and particularly about the intensity of light emanating from a patients tissue over time, may be transmitted from encoder 42 to a decoder 74. These signals may include, for example, encoded information relating to patient characteristics. Decoder 74 may translate these signals to enable the microprocessor to determine the thresholds based on algorithms or look-up tables stored in ROM 52. User inputs 56 may be used to enter information about the patient, such as age, weight, height, diagnosis, medications, treatments, and so forth. In an embodiment, display 20 may exhibit a list of values which may generally apply to the patient, such as, for example, age ranges or medication families, which the user may select using user inputs 56.

The optical signal through the tissue can be degraded by noise, among other sources. One source of noise is ambient light that reaches the light detector. Another source of noise is electromagnetic coupling from other electronic instruments. Movement of the patient also introduces noise and affects the signal. For example, the contact between the detector and the skin, or the emitter and the skin, can be temporarily disrupted when movement causes either to move away from the skin. In addition, because blood is a fluid, it responds differently than the surrounding tissue to inertial effects, thus resulting in momentary changes in volume at the point to which the oximeter probe is attached.

Noise (e.g., from patient movement) can degrade a pulse oximetry signal relied upon by a physician, without the physician's awareness. This is especially true if the monitoring of the patient is remote, the motion is too small to be observed, or the doctor is watching the instrument or other parts of the patient, and not the sensor site. Processing pulse oximetry (i.e., PPG) signals may involve operations that reduce the amount of noise present in the signals or otherwise identify noise components in order to prevent them from affecting measurements of physiological parameters derived from the PPG signals.

It will be understood that the present disclosure is applicable to any suitable signals and that PPG signals are used merely for illustrative purposes. Those skilled in the art will recognize that the present disclosure has wide applicability to other signals including, but not limited to other biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

In one embodiment, a PPG signal may be transformed using a continuous wavelet transform. Information derived from the transform of the PPG signal (i.e., in wavelet space) may be used to provide measurements of one or more physiological parameters.

The continuous wavelet transform of a signal x(t) in accordance with the present disclosure may be defined as $$T(a, b) = \frac{1}{\sqrt{a}} \int_{-\infty}^{+\infty} x(t)\psi^*\left(\frac{t-b}{a}\right) dt \qquad (9)$$

where $\psi^*(t)$ is the complex conjugate of the wavelet function $\psi(t)$, a is the dilation parameter of the wavelet and b is the location parameter of the wavelet. The transform given by equation (9) may be used to construct a representation of a signal on a transform surface. The transform may be regarded as a time-scale representation. Wavelets are composed of a range of frequencies, one of which may be denoted as the characteristic frequency of the wavelet, where the characteristic frequency associated with the wavelet is inversely proportional to the scale a. One example of a characteristic frequency is the dominant frequency. Each scale of a particular wavelet may have a different characteristic frequency. The underlying mathematical detail required for the implementation within a time-scale can be found, for example, in Paul S. Addison, The Illustrated Wavelet Transform Handbook (Taylor & Francis Group 2002), which is hereby incorporated by reference herein in its entirety.

The continuous wavelet transform decomposes a signal using wavelets, which are generally highly localized in time. The continuous wavelet transform may provide a higher resolution relative to discrete transforms, thus providing the ability to garner more information from signals than typical frequency transforms such as Fourier transforms (or any other spectral techniques) or discrete wavelet transforms. Continuous wavelet transforms allow for the use of a range of wavelets with scales spanning the scales of interest of a signal such that small scale signal components correlate well with the smaller scale wavelets and thus manifest at high energies at smaller scales in the transform. Likewise, large scale signal components correlate well with the larger scale wavelets and thus manifest at high energies at larger scales in the transform. Thus, components at different scales may be separated and extracted in the wavelet transform domain. Moreover, the use of a continuous range of wavelets in scale and time position allows for a higher resolution transform than is possible relative to discrete techniques.

In addition, transforms and operations that convert a signal or any other type of data into a spectral (i.e., frequency) domain necessarily create a series of frequency transform values in a two-dimensional coordinate system where the two dimensions may be frequency and, for example, amplitude. For example, any type of Fourier transform would generate such a two-dimensional spectrum. In contrast, wavelet transforms, such as continuous wavelet transforms, are required to be defined in a three-dimensional coordinate system and generate a surface with dimensions of time, scale and, for example, amplitude. Hence, operations performed in a spectral domain cannot be performed in the wavelet domain; instead the wavelet surface must be transformed into a spectrum (i.e., by performing an inverse wavelet transform to convert the wavelet surface into the time domain and then performing a spectral transform from the time domain). Conversely, operations performed in the wavelet domain cannot be performed in the spectral domain; instead a spectrum must first be transformed into a wavelet surface (i.e., by performing an inverse spectral transform to convert the spectral domain into the time domain and then performing a wavelet transform from the time domain). Nor does a cross-section of the three-dimensional wavelet surface along, for example, a particular point in time equate to a frequency spectrum upon which spectral-based techniques may be used. At least because wavelet space includes a time dimension, spectral techniques and wavelet techniques are not interchangeable. It will be understood that converting a system that relies on spectral domain processing to one that relies on wavelet space processing would require significant and fundamental modifications to the system in order to accommodate the wavelet space processing (e.g., to derive a representative energy value for a signal or part of a signal requires integrating twice, across time and scale, in the wavelet domain while, conversely, one integration across frequency is required to derive a representative energy value from a spectral domain). As a further example, to reconstruct a temporal signal requires integrating twice, across time and scale, in the wavelet domain while, conversely, one integration across frequency is required to derive a temporal signal from a spectral domain. It is well known in the art that, in addition to or as an alternative to amplitude, parameters such as energy density, modulus, phase, among others may all be generated using such transforms and that these parameters have distinctly different contexts and meanings when defined in a two-dimensional frequency coordinate system rather than a three-dimensional wavelet coordinate system. For example, the phase of a Fourier system is calculated with respect to a single origin for all frequencies while the phase for a wavelet system is unfolded into two dimensions with respect to a wavelet's location (often in time) and scale.

The energy density function of the wavelet transform, the scalogram, is defined as $$S(a,b) = |T(a,b)|^2 \qquad (10)$$

where '| |' is the modulus operator. The scalogram may be rescaled for useful purposes. One common rescaling is defined as $$S_R(a, b) = \frac{|T(a, b)|^2}{a} \qquad (11)$$

and is useful for defining ridges in wavelet space when, for example, the Morlet wavelet is used. Ridges are defined as the locus of points of local maxima in the plane. Any reasonable definition of a ridge may be employed in the method. Also included as a definition of a ridge herein are paths displaced from the locus of the local maxima. A ridge associated with only the locus of points of local maxima in the plane are labeled a "maxima ridge".

For implementations requiring fast numerical computation, the wavelet transform may be expressed as an approximation using Fourier transforms. Pursuant to the convolution theorem, because the wavelet transform is the cross-correlation of the signal with the wavelet function, the wavelet transform may be approximated in terms of an inverse FFT of the product of the Fourier transform of the signal and the Fourier transform of the wavelet for each required a scale and then multiplying the result by $\sqrt{a}$.

In the discussion of the technology which follows herein, the "scalogram" may be taken to include all suitable forms of rescaling including, but not limited to, the original unsealed wavelet representation, linear rescaling, any power of the modulus of the wavelet transform, or any other suitable rescaling. In addition, for purposes of clarity and conciseness, the term "scalogram" shall be taken to mean the wavelet transform, T(a,b) itself, or any part thereof. For example, the real part of the wavelet transform, the imaginary part of the wavelet transform, the phase of the wavelet transform, any other suitable part of the wavelet transform, or any combination thereof is intended to be conveyed by the term "scalogram".

A scale, which may be interpreted as a representative temporal period, may be converted to a characteristic frequency of the wavelet function. The characteristic frequency associated with a wavelet of arbitrary a scale is given by $$f = \frac{f_c}{a} \quad (12)$$

where $f_c$, the characteristic frequency of the mother wavelet (i.e., at a=1), becomes a scaling constant and f is the representative or characteristic frequency for the wavelet at arbitrary scale a.

Any suitable wavelet function may be used in connection with the present disclosure. One of the most commonly used complex wavelets, the Morlet wavelet, is defined as:

$$\psi(t) = \pi^{-1/4}(e^{i2\pi f_0 t} - e^{-(2\pi f_0)^2/2})e^{-t^2/2} \quad (13)$$

where $f_0$ is the central frequency of the mother wavelet. The second term in the parenthesis is known as the correction term, as it corrects for the non-zero mean of the complex sinusoid within the Gaussian window. In practice, it becomes negligible for values of $f_0 \gg 0$ and can be ignored, in which case, the Morlet wavelet can be written in a simpler form as $$\psi(t) = \frac{1}{\pi^{1/4}} e^{i2\pi f_0 t} e^{-t^2/2} \quad (14)$$

This wavelet is a complex wave within a scaled Gaussian envelope. While both definitions of the Morlet wavelet are included herein, the function of equation (14) is not strictly a wavelet as it has a non-zero mean (i.e., the zero frequency term of its corresponding energy spectrum is non-zero). However, it will be recognized by those skilled in the art that equation (14) may be used in practice with $f_0 \gg 0$ with minimal error and is included (as well as other similar near wavelet functions) in the definition of a wavelet herein. A more detailed overview of the underlying wavelet theory, including the definition of a wavelet function, can be found in the general literature. Discussed herein is how wavelet transform features may be extracted from the wavelet decomposition of signals. For example, wavelet decomposition of PPG signals may be used to provide clinically useful information within a medical device.

Figure 3B:
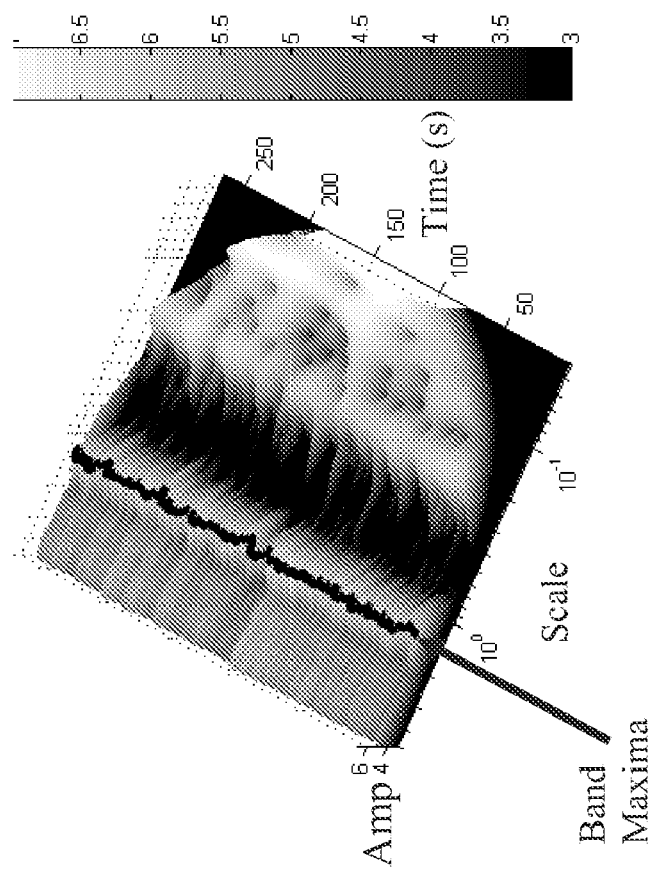
FIGS. 3(a) and 3(b) show illustrative views of a scalogram derived from a PPG signal in accordance with an embodiment.
Figure 3A:
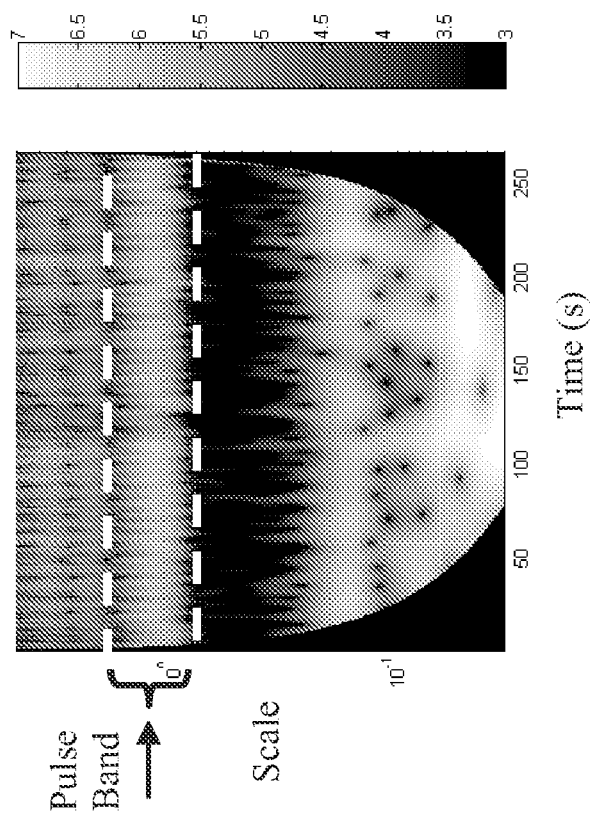

Pertinent repeating features in a signal give rise to a time-scale band in wavelet space or a rescaled wavelet space. For example, the pulse component of a PPG signal produces a dominant band in wavelet space at or around the pulse frequency. FIGS. 3(a) and (b) show two views of an illustrative scalogram derived from a PPG signal, according to an embodiment. The figures show an example of the band caused by the pulse component in such a signal. The pulse band is located between the dashed lines in the plot of FIG. 3(a). The band is formed from a series of dominant coalescing features across the scalogram. This can be clearly seen as a raised band across the transform surface in FIG. 3(b) located within the region of scales indicated by the arrow in the plot (corresponding to 60 beats per minute). The maxima of this band with respect to scale is the ridge. The locus of the ridge is shown as a black curve on top of the band in FIG. 3(b). By employing a suitable rescaling of the scalogram, such as that given in equation (11), the ridges found in wavelet space may be related to the instantaneous frequency of the signal. In this way, the pulse rate may be obtained from the PPG signal. Instead of rescaling the scalogram, a suitable predefined relationship between the scale obtained from the ridge on the wavelet surface and the actual pulse rate may also be used to determine the pulse rate.

By mapping the time-scale coordinates of the pulse ridge onto the wavelet phase information gained through the wavelet transform, individual pulses may be captured. In this way, both times between individual pulses and the timing of components within each pulse may be monitored and used to detect heart beat anomalies, measure arterial system compliance, or perform any other suitable calculations or diagnostics. Alternative definitions of a ridge may be employed. Alternative relationships between the ridge and the pulse frequency of occurrence may be employed.

Figure 3C:
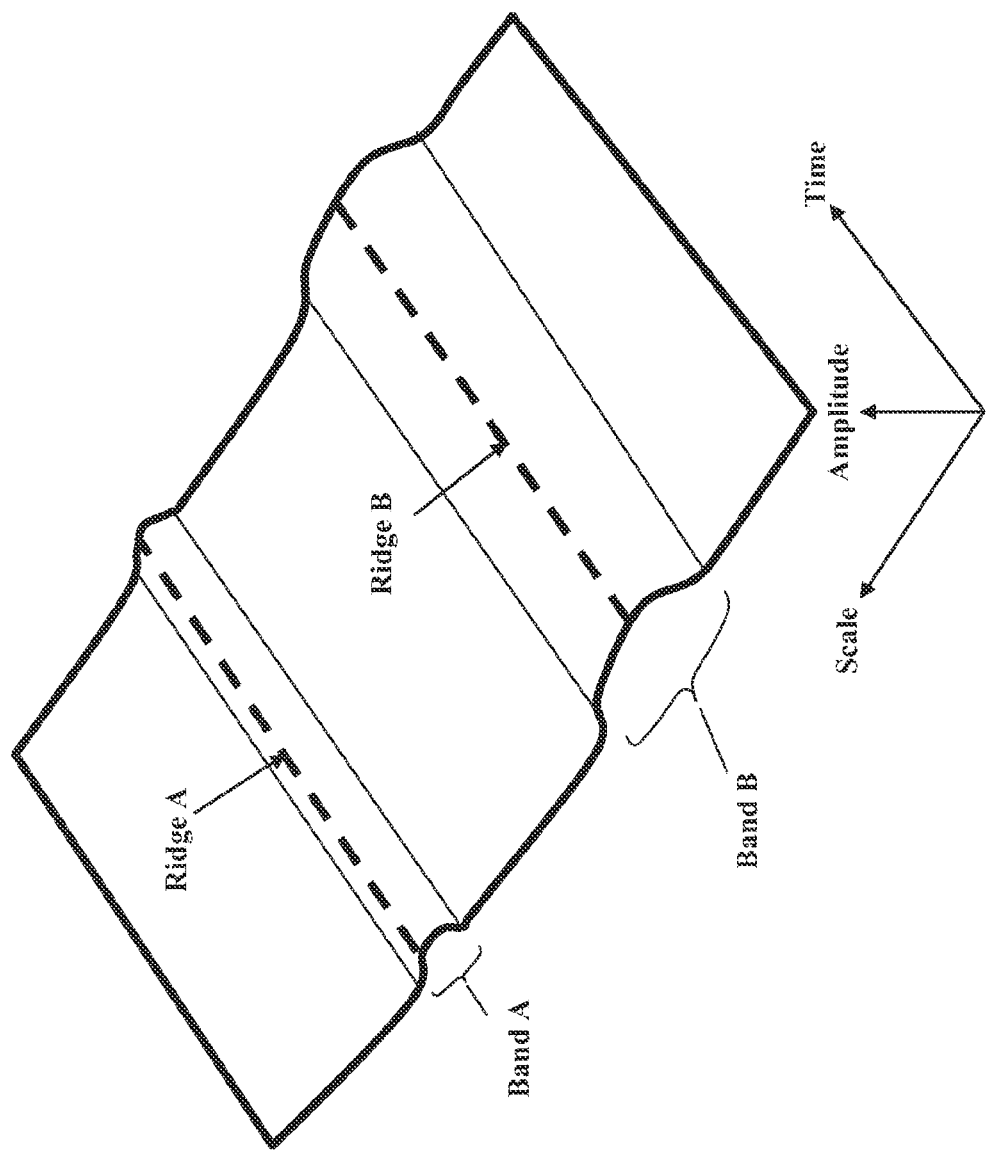
FIG. 3(c) shows an illustrative scalogram derived from a signal containing two pertinent components in accordance with an embodiment.
Figure 3D:
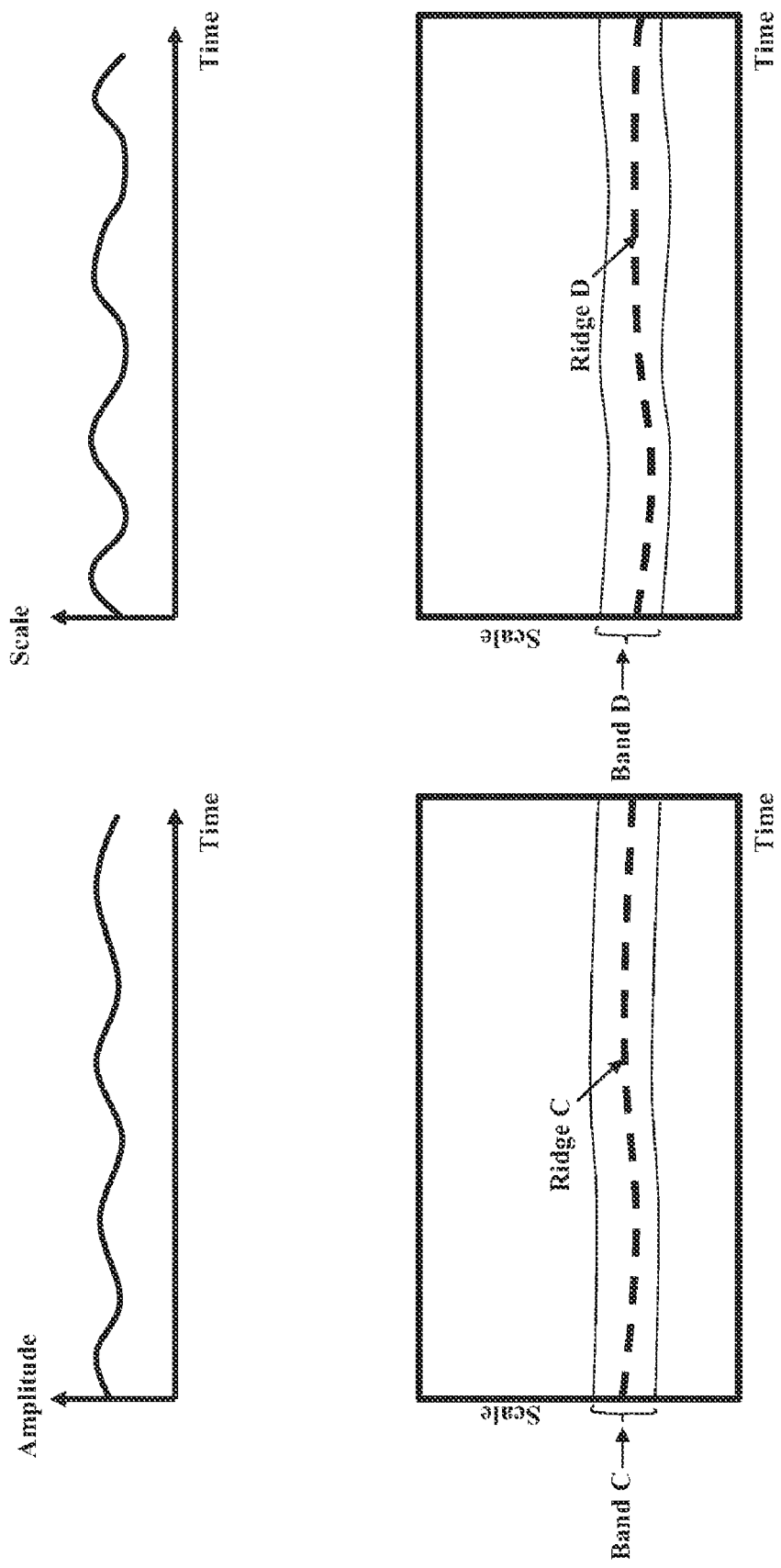
FIG. 3(d) shows an illustrative schematic of signals associated with a ridge in FIG. 3(c) and illustrative schematics of a further wavelet decomposition of these newly derived signals in accordance with an embodiment.

As discussed above, pertinent repeating features in the signal give rise to a time-scale band in wavelet space or a rescaled wavelet space. For a periodic signal, this band remains at a constant scale in the time-scale plane. For many real signals, especially biological signals, the band may be non-stationary; varying in scale, amplitude, or both over time. FIG. 3(c) shows an illustrative schematic of a wavelet transform of a signal containing two pertinent components leading to two bands in the transform space, according to an embodiment. These bands are labeled band A and band B on the three-dimensional schematic of the wavelet surface. In this embodiment, the band ridge is defined as the locus of the peak values of these bands with respect to scale. For purposes of discussion, it may be assumed that band B contains the signal information of interest. This will be referred to as the "primary band". In addition, it may be assumed that the system from which the signal originates, and from which the transform is subsequently derived, exhibits some form of coupling between the signal components in band A and band B. When noise or other erroneous features are present in the signal with similar spectral characteristics of the features of band B then the information within band B can become ambiguous (i.e., obscured, fragmented or missing). In this case, the ridge of band A may be followed in wavelet space and extracted either as an amplitude signal or a scale signal which will be referred to as the "ridge amplitude perturbation" (RAP) signal and the "ridge scale perturbation" (RSP) signal, respectively. The RAP and RSP signals may be extracted by projecting the ridge onto the time-amplitude or time-scale planes, respectively. The top plots of FIG. 3(d) show a schematic of the RAP and RSP signals associated with ridge A in FIG. 3(c). Below these RAP and RSP signals are schematics of a further wavelet decomposition of these newly derived signals. This secondary wavelet decomposition allows for information in the region of band B in FIG. 3(c) to be made available as band C and band D. The ridges of bands C and D may serve as instantaneous time-scale characteristic measures of the signal components causing bands C and D. This technique, which will be referred to herein as secondary wavelet feature decoupling (SWFD), may allow information concerning the nature of the signal components associated with the underlying physical process causing the primary band B (FIG. 3(c)) to be extracted when band B itself is obscured in the presence of noise or other erroneous signal features.

In some instances, an inverse continuous wavelet transform may be desired, such as when modifications to a scalogram (or modifications to the coefficients of a transformed signal) have been made in order to, for example, remove artifacts. In one embodiment, there is an inverse continuous wavelet transform which allows the original signal to be recovered from its wavelet transform by integrating over all scales and locations, a and b:

$$x(t) = \frac{1}{C_g} \int_{-\infty}^{\infty} \int_0^{\infty} T(a,b) \frac{1}{\sqrt{a}} \psi\left(\frac{t-b}{a}\right) \frac{da\,db}{a^2} \quad (15)$$

which may also be written as:

$$x(t) = \frac{1}{C_g} \int_{-\infty}^{\infty} \int_0^{\infty} T(a,b) \psi_{a,b}(t) \frac{da\,db}{a^2} \quad (16)$$

where $C_g$ is a scalar value known as the admissibility constant. It is wavelet type dependent and may be calculated from:

$$C_g = \int_0^{\infty} \frac{|\hat{\psi}(f)|^2}{f} df \quad (17)$$

Figure 3E:
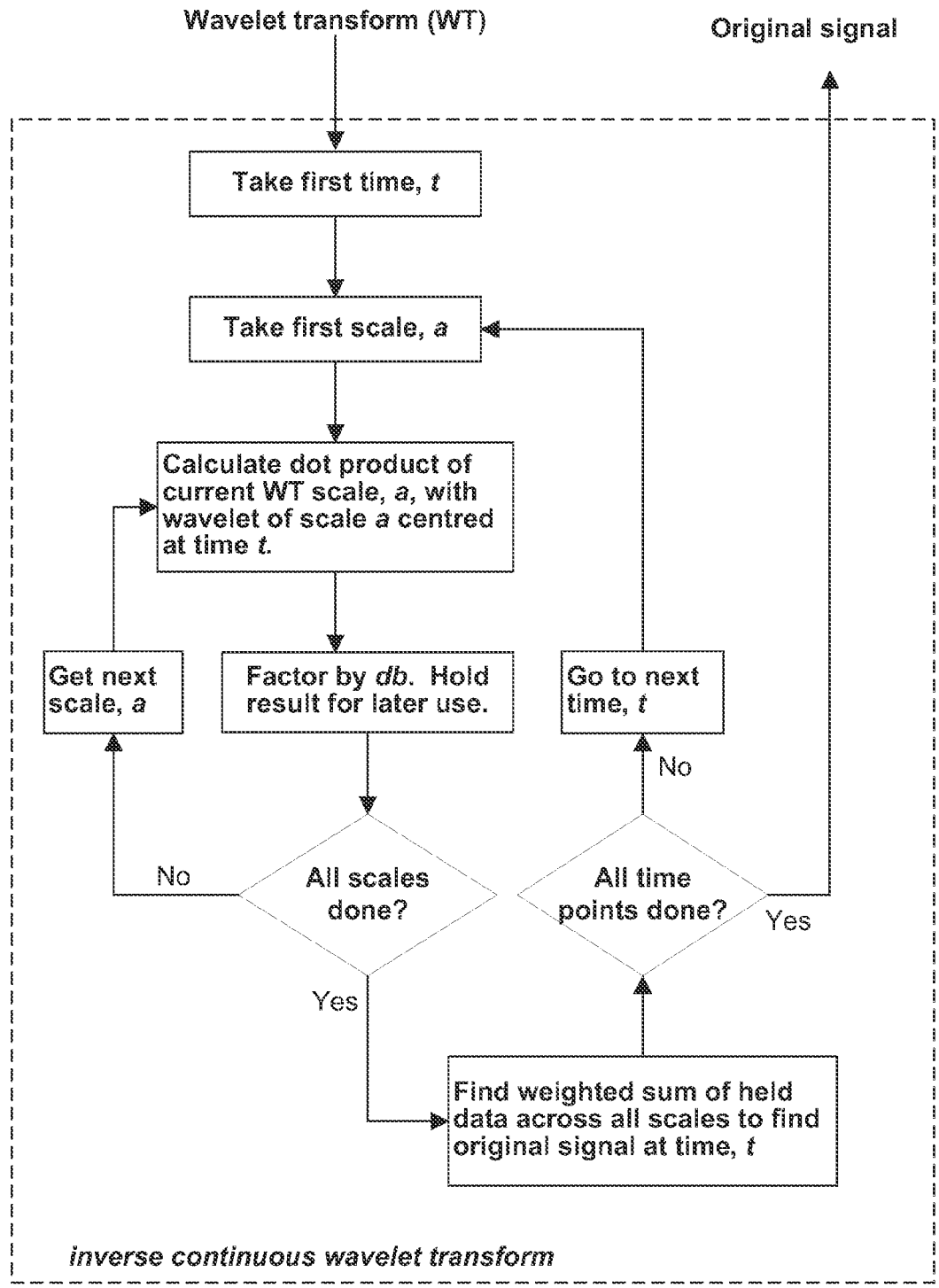
FIGS. 3(e) and 3(f) are flow charts of illustrative steps involved in performing an inverse continuous wavelet transform in accordance with embodiments.
Figure 3F:
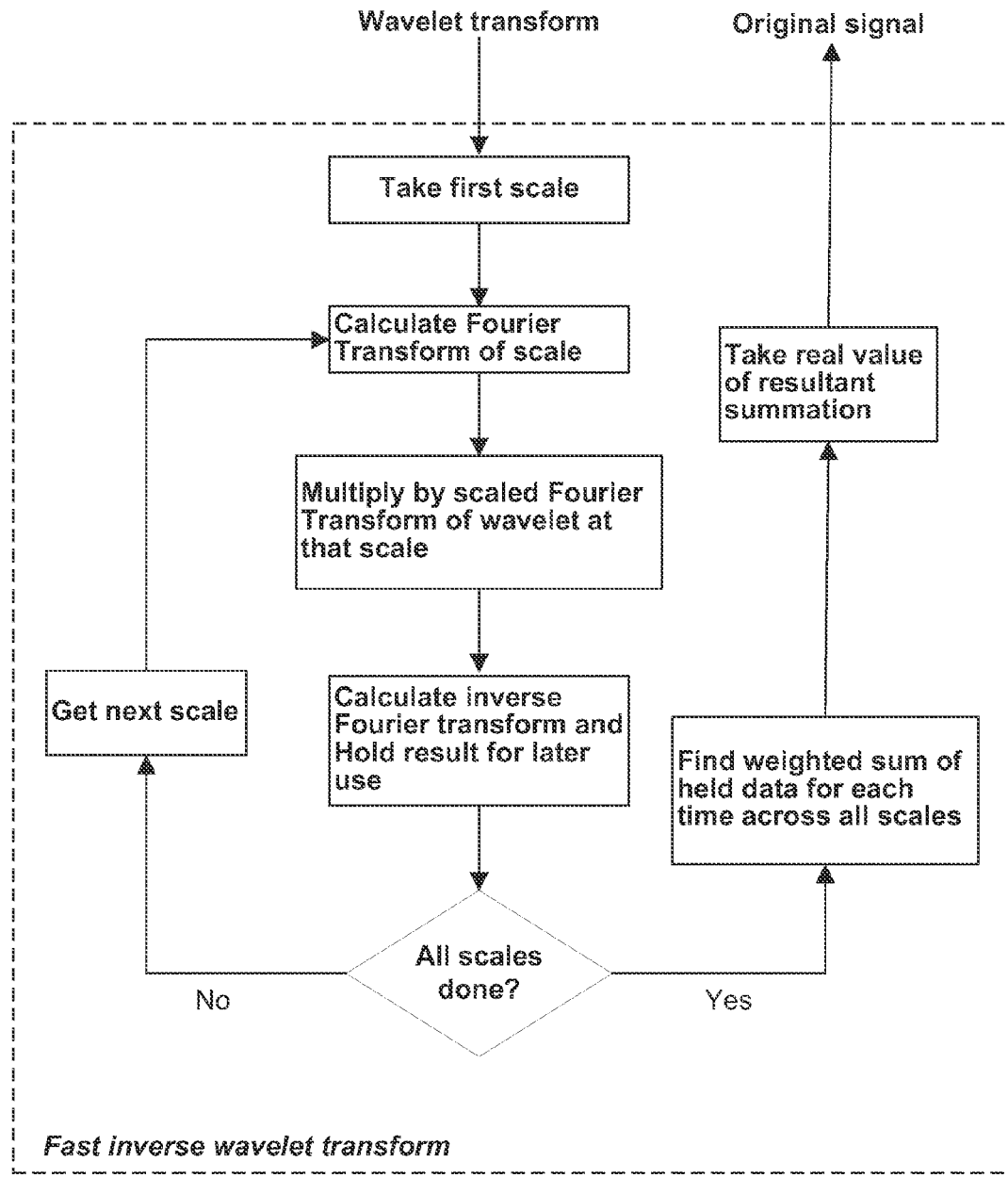

FIG. 3(e) is a flow chart of illustrative steps that may be taken to perform an inverse continuous wavelet transform in accordance with the above discussion. An approximation to the inverse transform may be made by considering equation (15) to be a series of convolutions across scales. It shall be understood that there is no complex conjugate here, unlike for the cross correlations of the forward transform. As well as integrating over all of a and b for each time t, this equation may also take advantage of the convolution theorem which allows the inverse wavelet transform to be executed using a series of multiplications. FIG. 3(f) is a flow chart of illustrative steps that may be taken to perform an approximation of an inverse continuous wavelet transform. It will be understood that any other suitable technique for performing an inverse continuous wavelet transform may be used in accordance with the present disclosure.

Figure 4:
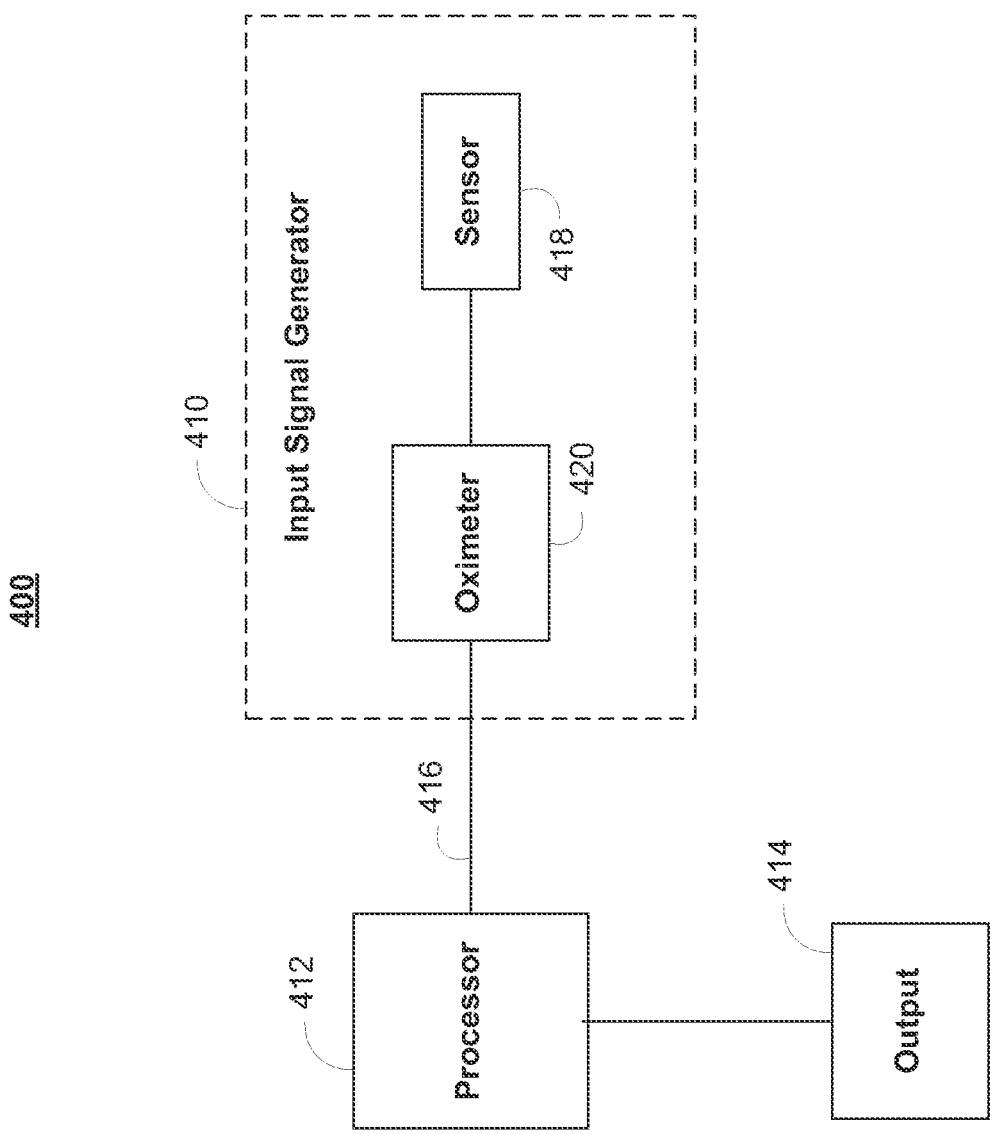
FIG. 4 is a block diagram of an illustrative continuous wavelet processing system in accordance with some embodiments.

FIG. 4 is an illustrative continuous wavelet processing system in accordance with an embodiment. In this embodiment, input signal generator 410 generates an input signal 416. As illustrated, input signal generator 410 may include oximeter 420 coupled to sensor 418, which may provide as input signal 416, a PPG signal. It will be understood that input signal generator 410 may include any suitable signal source, signal generating data, signal generating equipment, or any combination thereof to produce signal 416. Signal 416 may be any suitable signal or signals, such as, for example, biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

In this embodiment, signal 416 may be coupled to processor 412. Processor 412 may be any suitable software, firmware, and/or hardware, and/or combinations thereof for processing signal 416. For example, processor 412 may include one or more hardware processors (e.g., integrated circuits), one or more software modules, computer-readable media such as memory, firmware, or any combination thereof Processor 412 may, for example, be a computer or may be one or more chips (i.e., integrated circuits). Processor 412 may perform the calculations associated with the continuous wavelet transforms of the present disclosure as well as the calculations associated with any suitable interrogations of the transforms. Processor 412 may perform any suitable signal processing of signal 416 to filter signal 416, such as any suitable band-pass filtering, adaptive filtering, closed-loop filtering, and/or any other suitable filtering, and/or any combination thereof.

Processor 412 may be coupled to one or more memory devices (not shown) or incorporate one or more memory devices such as any suitable volatile memory device (e.g., RAM, registers, etc.), non-volatile memory device (e.g., ROM, EPROM, magnetic storage device, optical storage device, flash memory, etc.), or both. The memory may be used by processor 412 to, for example, store data corresponding to a continuous wavelet transform of input signal 416, such as data representing a scalogram. In one embodiment, data representing a scalogram may be stored in RAM or memory internal to processor 412 as any suitable three-dimensional data structure such as a three-dimensional array that represents the scalogram as energy levels in a time-scale plane. Any other suitable data structure may be used to store data representing a scalogram.

Processor 412 may be coupled to output 414. Output 414 may be any suitable output device such as, for example, one or more medical devices (e.g., a medical monitor that displays various physiological parameters, a medical alarm, or any other suitable medical device that either displays physiological parameters or uses the output of processor 412 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

It will be understood that system 400 may be incorporated into system 10 (FIGS. 1 and 2) in which, for example, input signal generator 410 may be implemented as parts of sensor 12 and monitor 14 and processor 412 may be implemented as part of monitor 14.

Basis functions may also be used in accordance with the disclosure. Such basis functions may be restricted such that no function can be represented as a linear combination of the other functions within the basis set. In other words, the basis set may be a linearly independent spanning set (e.g., the sinusoidal Fourier basis set). This property may have advantages in such applications as signal compression where its use often restricts the number of coefficients necessary to describe a signal.

Basis functions may also be used to determine physiological information from a physiological signal. The signal may be first processed to determine a set of basis function waveforms to be used for further processing. For example, the basis function waveforms may be sinusoids having frequencies about a particular frequency or frequencies of interest. When determining oxygen saturation from PPG signals, the set of basis function waveforms may have frequencies within the expected range of frequencies or at an estimated frequency of the pulse rate. A window may be defined around the expected range of frequencies or estimated frequency of the pulse rate. This window may include the only set of frequencies which are processed by the basis functions to determine physiological information. The basis function waveforms may be generated according to this defined window, the maximum or minimum magnitude of the original signal, the amount of noise present in the original signal, any other characteristic of the original signal or any combination thereof. The generated basis function waveforms may be collectively referred to as a basis function subset or subsets.

For each basis function waveform generated, a cancellation component may be used to subtract the basis function waveform from the original signal, thereby creating a remainder signal. Alternatively, each basis function waveform may be used to generate corresponding basis function components of the original signal. For example, the cancellation components may be generated according to the inner product of the original signal and each basis function of a generated basis function subset. The cancellation components may be applied to the original signal iteratively between other steps of processing the original signal. The iterative cancellation may be about a particular area of interest in the original. An area of interest in the PPG signal may be a particular frequency or range of frequencies about a unique characteristic within the signal, such as a frequency or range of frequencies about an estimate of the pulse rate. Alternatively, an area of interest in the PPG signal may be a particular time or range of time about a unique event in the signal, such as a time in which physiological information is determined. The particular area of interest may be selected according to the criteria for basis waveform generation mentioned above. Alternatively, the cancellation components may be applied once about an area of interest in the original signal. The resulting remainder signals or basis function components may be analyzed to generate an index associated with an optimization of the remainder signals or basis function components. A basis function waveform may be generated based on the index and used to select a component from the original signal. The selected component may be used to determine physiological information. For example, oxygen saturation may be determined by taking a magnitude ratio of the selected components of the red and infrared PPG signals.

Continuous wavelet transforms, in contrast to the above described basis functions, have inherent redundancy by way of their high degree of resolution in location and scale. This redundancy often helps in the detection and identification of features within the signal.

In an embodiment, wavelet transforms and basis function may be used together to determine physiological information. Basis functions typically have faster indexing and the lower computational loads (at preselected indexes). Continuous wavelet transforms have good feature identification and denoising strengths (at preselected scales and times). Therefore, collectively, basis functions and continuous wavelet transforms may provide an optimized system for determining physiological information.

In an embodiment, basis function generation and an iterative cancellation process may be used to identify regions of a signal with the morphology of interest while the wavelet transform may focus on these regions to determine or filter the actual information of interest. For example, a sinusoidal basis set may be generated, and an iterative cancellation procedure about an estimate of the pulse rate may be used to identify a nominal frequency of interest for the derivation of oxygen saturation. The wavelet transform may then be performed at scales with characteristic frequencies about this frequency of interest. The maxima ridge in the scalogram proximal to these scales of interest may then be used to determine physiological information such as pulse rate, respiration rate, and oxygen saturation.

In an embodiment, the wavelet transform may be used to identify regions of a signal with the morphology of interest while basis function generation and an iterative cancellation process may be used to focus on these regions to determine or filter the actual information of interest. For example, a wavelet transform may be performed at scales with characteristic frequencies in the signal. A window about a maxima ridge in the scalogram proximal to an estimate of the pulse rate may be identified as a range of frequency of interest for the derivation of oxygen saturation. A sinusoidal basis set may be generated, and an iterative cancellation procedure about the identified area of interest may then be used to filter out actual information of interest. The area of interest may then be further processed to determine physiological information such as pulse rate, respiration rate, and oxygen saturation.

In an embodiment, basis functions and continuous wavelet transforms may be used concurrently and their results compared to determine optimized information or a confidence metric for the determined information. For example, a sinusoidal basis set may be generated, and an iterative cancellation procedure about an estimate of the pulse rate may be used, to identify a nominal frequency of interest for the derivation of oxygen saturation. Concurrently, a scalogram may be derived for scales with characteristic frequencies about an estimate of the pulse rate. The maxima ridge in the scalogram proximal to this pulse rate estimate may then be used to determine physiological information such as pulse rate, respiration rate, and oxygen saturation. An optimized value for oxygen saturation may be taken as an average of those derived by the two methods. A confidence measure may be derived from the difference between those values calculated using the two methods.

The continuous wavelet transform method may provide a more accurate calculation of oxygen saturation due to its ability to track changes in pulse rate (changes in the scale of interest) and its ability to ignore regions of scalogram associated with temporally discrete artifact (spikes). Both these features are due to the ability of the continuous wavelet transform to accurately resolve in the time domain when compared to spectral averaging techniques.

In an embodiment, systems 400 (FIG. 4) and/or 10 (FIGS. 1 and 2) may use continuous wavelet transform (CWT) techniques for calculating pulse rate. The pulse component of a PPG signal may produce a dominant band in a scalogram. The pulse rate may be calculated, for example, using a CWT technique by generating a scalogram from a PPG signal, following or identifying the ridge of the pulse band, identifying a scale corresponding to the ridge, and selecting the pulse rate to be the characteristic frequency of the identified scale.

Respiration rate may also be calculated using CWT techniques. The respiration component of a PPG signal may exhibit itself as a band of scales in a scalogram similar to the pulse band. Therefore, the respiration rate may be calculated, for example, using a CWT technique by generating a scalogram from a PPG signal, following or identifying the ridge of the respiration band (e.g., located at scales lower than the scales where the typically more dominant pulse band occurs), identifying a scale corresponding to the ridge, and selecting the respiration rate to be the characteristic frequency of the identified scale. The respiration component of the PPG signal may also cause modulations of the pulse band. Thus, the respiration rate may also be calculated by performing a secondary wavelet decomposition of modulations (e.g., of RAP and RSP signals) of the pulse band. These and other CWT techniques for calculating respiration rate are described in detail in Addison et al. U.S. Pat. No. 7,035,679, Addison et al. U.S. Patent Publication No. 2006/0258921, and U.S. patent application Ser. No. 12/245,326, filed Oct. 3, 2008, entitled "Systems And Methods For Ridge Selection In Scalograms Of Signals," each of which is hereby incorporated by reference herein in its entirety.

The oxygen saturation may, for example, be determined using the methods described in Addison et al. U.S. Patent Publication No. 2006/0258921, published Nov. 16, 2006, which is incorporated by reference herein in its entirety.

Figure 5:
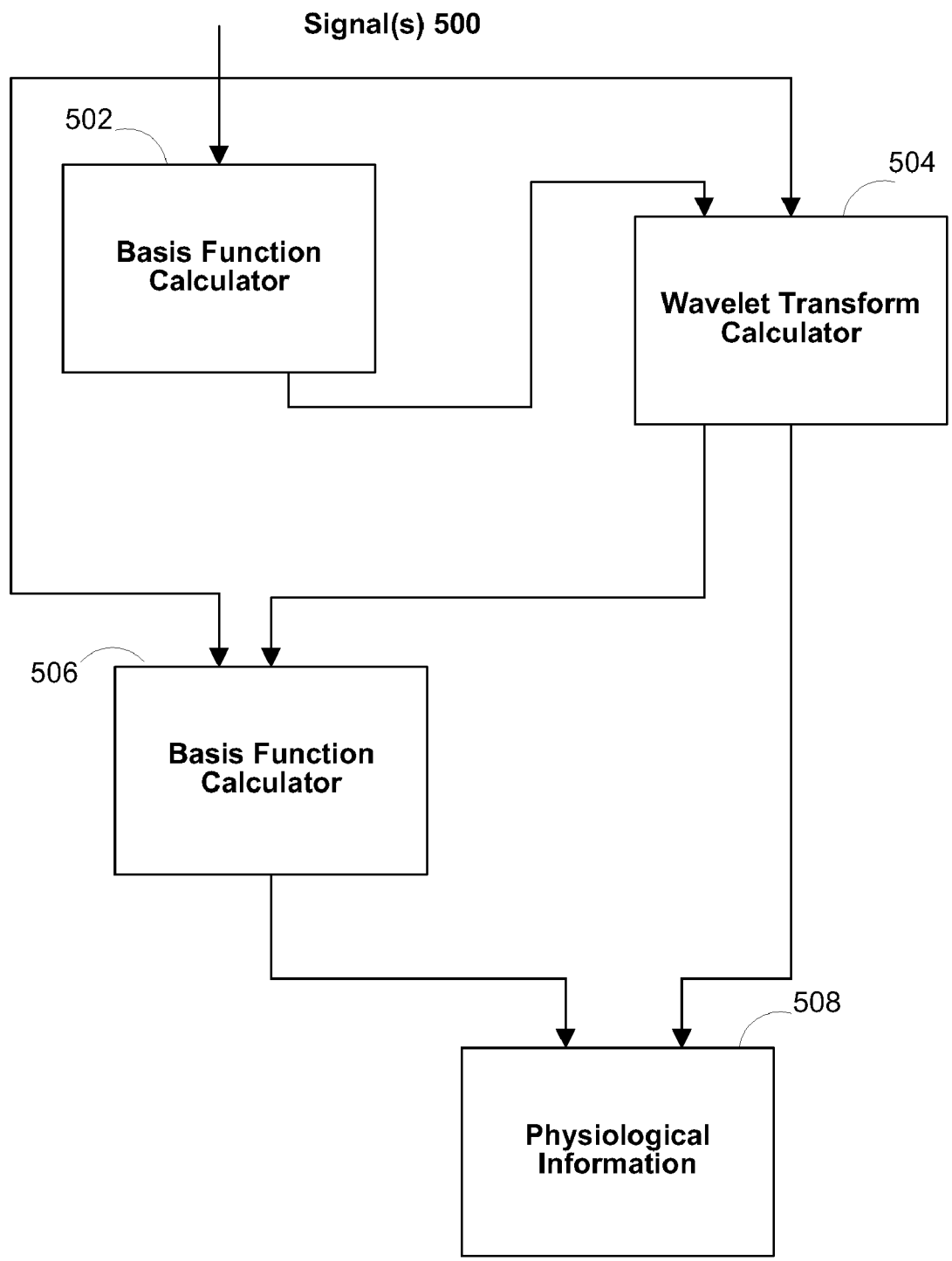
FIG. 5 shows a functional block diagram of a signal processor that performs basis functions and wavelet transforms.

FIG. 5 shows a functional block diagram of a signal processor that performs basis functions and continuous wavelet transforms. One or more signals 500 may be received at basis function calculator 502, wavelet transform calculator 504, and basis function calculator 506. Basis function calculator 502 may be used to determine one or more regions of interest of the received signal(s) 500 using any suitable basis functions. Basis function calculator 502 may output the one or more regions of interest to wavelet transform calculator 504.

Wavelet transform calculator 504 may perform a wavelet transform (e.g., a continuous wavelet transform) of the received signal(s) 500. In an embodiment, the wavelet transform may be generated at scales based on the regions of interest received from basis function calculator 502. For example, if basis function calculator 502 outputs a single frequency of interest, wavelet transform calculator 504 may perform a wavelet transform for a range of scales about the scale whose characteristic frequency is the frequency outputted from basis function calculator 502. Wavelet transform calculator 504 may determine physiological information from the wavelet transform. For example, if received signals 500 are red and infrared PPG signals, oxygen saturation may be computed by taking a ratio of the amplitudes of the pulse band from scalograms derived from the red and infrared wavelet transforms.

Wavelet transform calculator 504 may output the physiological information and any other suitable information to physiological information 508. Wavelet transform calculator 504 may also output information to basis function calculator 506. For example, wavelet transform calculator 504 may output the scale value at which the ratio was taken to calculate oxygen saturation or the characteristic frequency of the scale value.

Basis function calculator 506 may use the information received from wavelet transform calculator 504 to generate a basis function waveform. Wavelet transform calculator 504 may use the basis function waveform to generate a signal component of received signal(s) 500. The signal component may be used to determine physiological information such as oxygen saturation. Basis function calculator 506 may output the determined physiological information and any other suitable information to physiological information 508.

Physiological information 508 may generate optimized physiological information based at least in part on the physiological information received from wavelet transform calculator 504 and basis function calculator 506. In one approach, the optimized physiological information may be calculated by averaging the two received pieces of information. In another approach, the optimized physiological information may be calculated using a weighted average of the two received pieces of information. The weighting may be based in part on information received from calculators 504 and 506. Physiological information 508 may also generate a confidence indicator for the optimized physiological information. The confidence indicator may be based at least in part on the difference between the physiological information determined by basis function calculator 506 and wavelet transform calculator 504, on information received from basis function calculator 506 and/or wavelet transform calculator 504, on any other suitable information, or any combination thereof.

The functional block diagram of FIG. 5 is merely illustrative and any suitable changes may be made in accordance with the disclosure. For example, basis function calculator 502 may be optional. If basis function calculator 502 were removed, wavelet transform calculator 504 may generate a wavelet transform over a wider range of scales. As another example, basis function calculator 506 and physiological information 508 may be optional. In such a scenario, the optimal physiological information may be determined by wavelet transform calculator 504. As yet another example, the input to basis function calculator 506 from wavelet transform 504 may be optional. Therefore, basis function calculator 506 may determine the physiological information without using any information from wavelet transform calculator 504.

Figure 6:
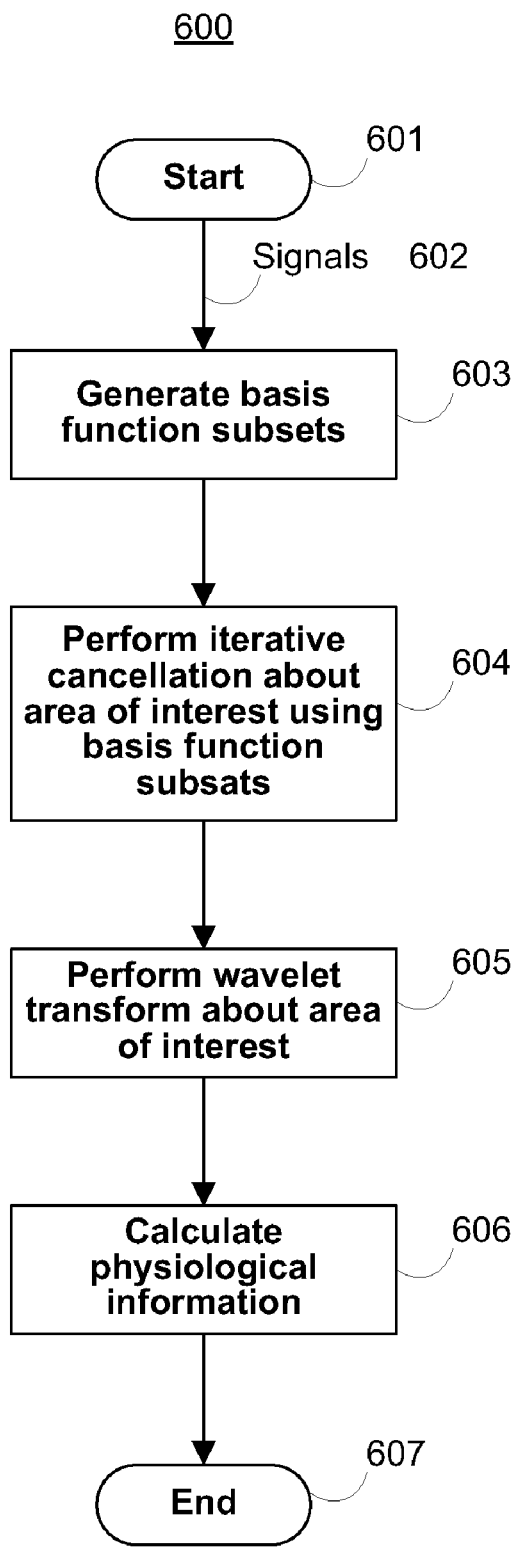
FIG. 6 is a flowchart of an embodiment of a process for determining physiological information from a PPG signal using basis functions and continuous wavelet transforms in accordance with an embodiment.

FIG. 6 is a flowchart of an embodiment of a process for determining physiological information from a PPG signal using basis functions and continuous wavelet transforms. Process 600 may begin at step 601. At step 603, one or more signals 602 may be received and basis function subsets may be generated. The basis function susbsets may be generated using, for example, basis function calculator 502 of FIG. 5. As discussed above with respect to basis function calculator 502, basis functions may be used to determine one or more areas of interest in frequency or in time in the received signals 602. At step 603, cancellation components may be generated based on the basis function subsets for use in subtracting the basis function waveforms from received signals 602. At step 604 iterative cancellation may be performed about an area of interest in the received signals 602. The area of interest may be a region of frequency in the received signals 602 in which there is an estimate of the pulse rate. The resulting signals may be analyzed to generate an index associated with an optimization of the basis function components. A basis function waveform may be generated based on the index and used to select a component from the signal. Then, at step 605 a wavelet transform may be performed at scales with characteristic frequencies about the area of interest in the resulting signal or selected component. The wavelet transformed may be performed using, for example, wavelet transform calculator 504 of FIG. 5. The maxima ridge in the scalogram of signals 602 proximal to these frequencies of interest may be identified, and then used at step 606 to determine physiological information such as pulse rate, respiration rate, and oxygen saturation. Process 600 may then advance to step 607 and end.

Figure 7:
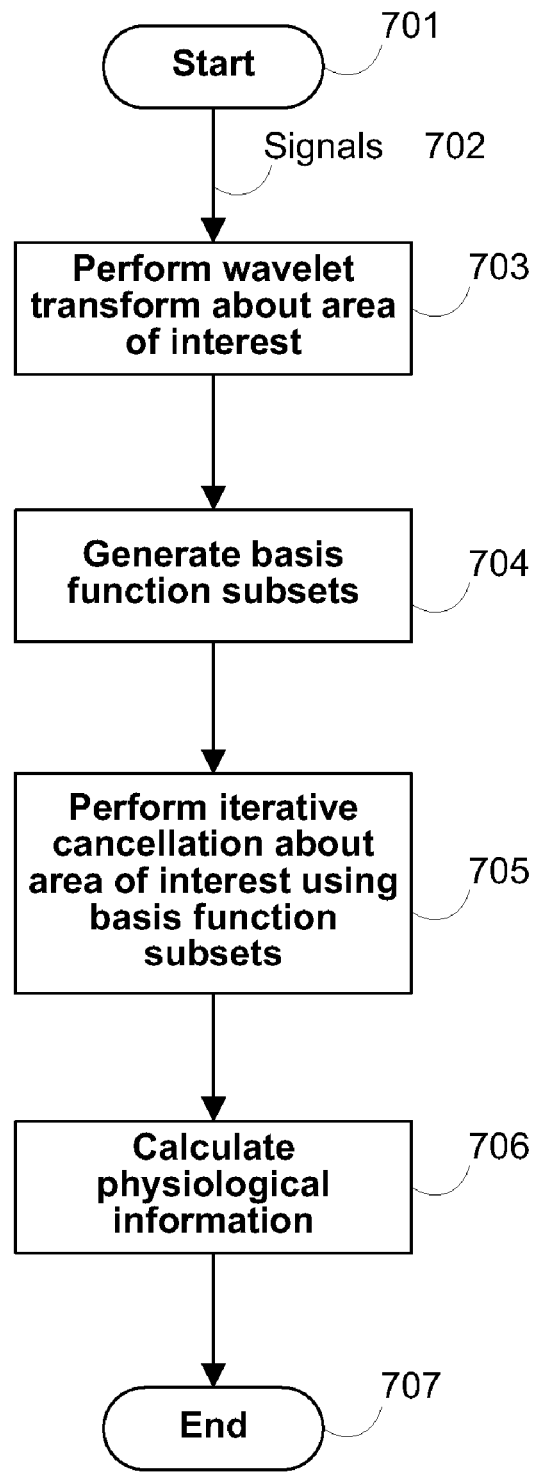
FIG. 7 is a flowchart of an embodiment of a process for determining physiological information from a PPG signal using basis functions and continuous wavelet transforms in accordance with an embodiment.

FIG. 7 is a flowchart of another embodiment of a process for determining physiological information from a PPG signal using basis functions and continuous wavelet transforms. Process 700 may begin at step 701. At step 703, one or more signals 702 may be received and wavelet transforms may be performed at scales with characteristic frequencies in the received signals 702. An area of interest in frequency or in time may be identified as a window in frequency or in time in the signals 702. For example, a window may be defined in frequency about a maxima ridge in the scalogram of received signals 702 in which there is an estimate of the pulse rate. The wavelet transform may be performed using, for example, wavelet transform calculator 504 of FIG. 5. At step 704 basis function subsets may be generated from the results of the continuous wavelet transform of 703 using, for example, basis function calculator 506 of FIG. 5. At step 704, cancellation components may be generated based on the basis function subsets for use in subtracting the basis function waveforms from received signals 702. At step 705 iterative cancellation may be performed about the area of interest in the received signals 702. The resulting signals may be a version of received signals 702 with a filtered area of interest. The filtered area of interest may then be used at step 706 to determine physiological information such as pulse rate, respiration rate, and oxygen saturation. Process 700 may then advance to step 707 and end.

Figure 8:
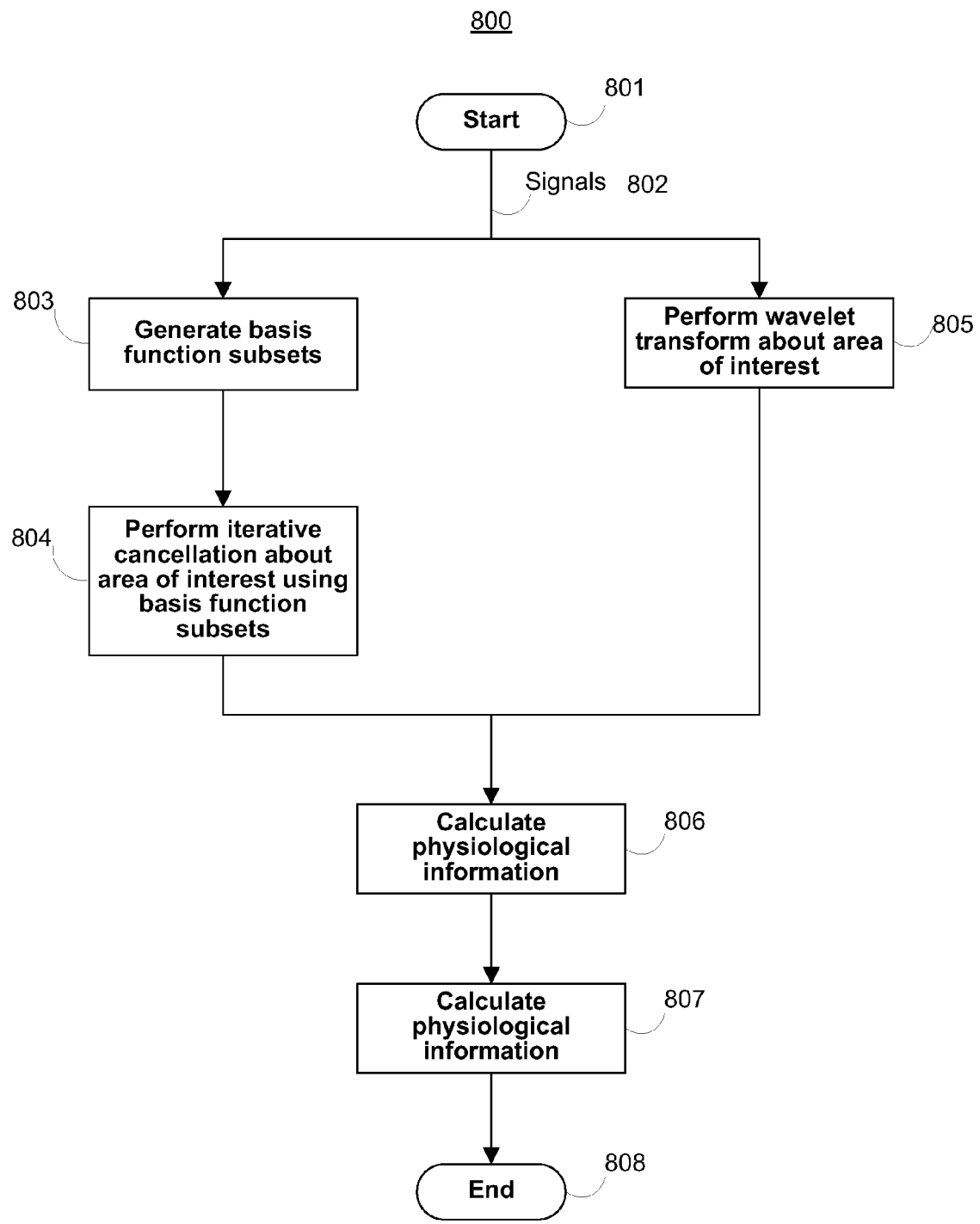
FIG. 8 is a flowchart of an embodiment of a process for determining physiological information from a PPG signal using basis functions and continuous wavelet transforms in accordance with an embodiment.

FIG. 8 is a flowchart of an embodiment of a process for determining physiological information from a PPG signal using basis functions and continuous wavelet transforms. Process 800 may begin at step 701. At steps 803 and 805, one or more signals 802 may be received. Basis function subsets may be generated at step 803 and used to determine one or more areas of interest in frequency or in time in the received signals 802. The basis function subsets may be generated using, for example, basis function calculator 502 or 506 of FIG. 5. At step 803, cancellation components may be generated based on the basis function subsets for use in subtracting the basis function waveforms from received signals 802. At step 804 iterative cancellation may be performed about an area of interest in the received signals 802. The area of interest may be a region of frequency in the received signals 802 in which there is an estimate of the pulse rate. The resulting signals may be a version of received signals 802 with a filtered area of interest. Concurrently, at step 805 a wavelet transform may be performed at scales with characteristic frequencies about the area of interest in received signals 802. The wavelet transformed may be performed using, for example, wavelet transform calculator 504 of FIG. 5. The maxima ridge in the scalogram of signals 802 proximal to these scales of interest may be identified. While steps 803-805 are illustrated as being performed substantially in parallel (e.g. by basis function calculators 502 or 506 of FIG. 5 and wavelet transform calculator 504 of FIG. 5), it should be understood that these steps may also be performed serially. At step 806, the results of the iterative cancellation process using basis functions and wavelet transform are combined. For example, a confidence measure may be derived from the information produced by the two separate methods. At step 807, physiological information may be determined based on the combined results. For example, an optimized value for oxygen saturation may be derived from the difference between the information produced by the two separate methods. Process 800 may then advance to step 908 and end.

The foregoing is merely illustrative of the principles of this disclosure and various modifications can be made by those skilled in the art without departing from the scope and spirit of the disclosure. The following numbered paragraphs may also describe various aspects of this disclosure.

What is claimed is:

1. A method for determining physiological information, comprising:
   using a processor for:
      receiving a signal;
      using a plurality of basis functions to generate information about the signal;
      performing a continuous wavelet transform of the signal for a plurality of scales selected based at least in part on the information generated using the plurality of basis functions; and
      determining the physiological information based at least in part on the wavelet transform.

2. The method of claim 1, wherein using the plurality of basis functions to generate information about the signal further comprises:
   generating a basis function subset based, at least in part, on the expected range of frequencies of a pulse rate signal; and
   generating cancellation components based, at least in part, on the basis function subset.

3. The method of claim 2, further comprising performing an iterative cancellation process using the cancellation components and the signal to generate a plurality of remainder signals.

4. The method of claim 3, wherein generating a basis function subset further comprises generating basis function components according to the inner product of the original signal and each basis function of the basis function subset.

5. The method of claim 3, further comprising analyzing the plurality of remainder signals to generate a basis function index.

6. The method of claim 5, further comprising:
   generating a basis function waveform based, at least in part, on the basis function index; and
   selecting a component of interest from the basis function waveform.

7. The method of claim 6, wherein the physiological information is determined based, at least in part, on the selected component.

8. The method of claim 1, wherein the signal is a photoplethysmogram (PPG) signal.

9. A method for determining physiological information, comprising:
   using a processor for:
      receiving a signal;
      selecting an area of interest in the signal;
      performing a wavelet transform of the signal for a plurality of scales selected based at least in part on the area of interest;
      using a basis function to generate information about the signal based at least in part on the information generated using the wavelet transform; and
      determining the physiological information based at least in part on the basis function.

10. The method of claim 9, wherein the area of interest is a window in frequency about a maxima ridge in the signal proximal to an estimate of a pulse rate.

11. The method of claim 1, further comprising determining an optimized piece of physiological information based at least in part on the information generated by the basis functions and the wavelet transform.

12. The method of claim 11, further comprising calculating a confidence measure based on a difference between the information generated by the basis functions and the wavelet transform.

13. A system for determining physiological information, comprising:
   a plurality of basis function calculators configured to generate information about a signal;
   a wavelet transform calculator configured to perform a wavelet transform of the signal for a plurality of scales selected based at least in part on the information generated by the plurality of basis function calculators; and a processor configured to determine physiological information based at least in part on the wavelet transform.

14. The system of claim 13, wherein the plurality of basis function calculators are further configured to:

generate a basis function subset based, at least in part, on the basis function; and generate cancellation components based, at least in part, on the basis function subset.

15. The system of claim 14, wherein the plurality of basis function calculators are further configured to perform an iterative cancellation process using the cancellation components and the signal to generate a plurality of remainder signals.

16. A non-transitory computer-readable medium for use in determining physiological information from a signal, the non-transitory computer-readable medium having computer program instructions recorded thereon for:

using a plurality of basis functions to generate information about the signal;

performing a wavelet transform of the signal for a plurality of scaled selected based at least in part on the information generated using the plurality of basis functions; and determining the physiological information based at least in part on the wavelet transform.

17. The non-transitory computer-readable medium of claim 16, further comprising instructions for:

generating a basis subset based, at least in part, on the expected range of frequencies of a pulse rate signal; and generating cancellation components based, at least in part, on the basis function subset.

18. The non-transitory computer-readable medium of claim 17, further comprising instructions for performing an iterative cancellation process using the cancellation components and the signal to generate a plurality of remainder signals.

19. The non-transitory computer-readable medium of claim 18, further comprising instructions for analyzing the plurality of remainder signals to generate a basis function index.

* * * * *